United States Patent [19]
Dean, Jr. et al.

[11] Patent Number: 4,997,753
[45] Date of Patent: * Mar. 5, 1991

[54] WEIGHTED COLLAGEN MICROSPONGE FOR IMMOBILIZING BIOACTIVE MATERIAL

[75] Inventors: Robert C. Dean, Jr., Norwich, Vt.; Frederick H. Silver, Long Valley; Richard A. Berg, Lambertville, both of N.J.; Philip G. Phillips, Norwich, Vt.; Peter W. Runstadler, Jr., Hanover, N.H.

[73] Assignee: Verax Corporation, Hanover, N.H.

[ * ] Notice: The portion of the term of this patent subsequent to Aug. 29, 2005 has been disclaimed.

[21] Appl. No.: 393,656

[22] Filed: Aug. 14, 1989

Related U.S. Application Data

[63] Continuation of Ser. No. 719,881, Apr. 4, 1985, Pat. No. 4,861,714.

[51] Int. Cl.⁵ ............... C12P 21/00; C12N 11/02; C12N 5/02; C12N 1/20
[52] U.S. Cl. ............... 435/69.1; 435/172.1; 435/174; 435/176; 435/177; 435/240.23; 435/240.24; 435/240.26; 435/252.3; 435/70.21; 435/70.3; 436/548; 530/356; 935/60
[58] Field of Search ............... 435/68, 174, 176, 177, 435/240.23, 240.24, 240.26, 252.3, 170, 171, 172.1; 530/356; 436/548

[56] References Cited

U.S. PATENT DOCUMENTS

| | | |
|---|---|---|
| 3,242,055 | 3/1966 | De Lucia ............... 435/182 |
| 4,149,936 | 4/1979 | Messing et al. ............... 435/176 |
| 4,153,510 | 5/1979 | Messing et al. ............... 435/176 |
| 4,224,413 | 9/1980 | Burbidge ............... 435/284 |
| 4,266,029 | 5/1981 | Branner-Jorgensen ............... 435/174 |
| 4,703,108 | 10/1987 | Silver et al. ............... 530/356 |
| 4,837,285 | 6/1989 | Berg et al. ............... 530/356 |
| 4,861,714 | 10/1989 | Dean, Jr. et al. ............... 435/68 |
| 4,863,856 | 9/1989 | Dean, Jr. et al. ............... 435/240.24 X |

FOREIGN PATENT DOCUMENTS 0097907 1/1984 European Pat. Off. .

*Primary Examiner*—David M. Naff
*Attorney, Agent, or Firm*—Banner, Birch, McKie & Beckett

[57] ABSTRACT

Weighted collagen microsponges having a highly crosslinked collagen matrix are described suitable for use in culturing organisms in motive reactor systems. The microsponges have an open to the surface pore structure, and pore sizes and volumes suitable for immobilizing a variety of bioactive materials. The microsponges also have an average particle size in the range of about 100 to about 1000 microns and a specific gravity above about 1.05.

20 Claims, 2 Drawing Sheets

WEIGHTED COLLAGEN MICROSPONGE FOR IMMOBILIZING BIOACTIVE MATERIAL

This invention was made in the course of, or under, a contract with NIH. The government has rights to the invention pursuant to SBIR Grant No. CA37430.

This application is a continuation of application Ser. No. 719,881, filed Apr. 4, 1985, now U.S. Pat. No. 4,861,114.

BACKGROUND OF THE INVENTION

1. Field of the Invention

The present invention pertains to the art of immobilizing bioactive materials and particularly relates to a collagen microsponge for use in motive bioreactor systems. The present invention also relates to the art of culturing microorganisms and cells, hereinafter referred to collectively as organisms, and particularly relates to the culturing of organisms immobilized on microsponges in motive reactor systems as submerged suspensions.

2. Description of the Prior Art

Various arrangements for immobilizing bioactive materials are known. Solid supports have long been used for immobilizing microorganisms in the treatment of waste water and related fermentation processes. More recently, solid microcarriers have been used to obtain high cell densities in the culture of attachment-dependent cells. For example, microporous polymeric supports fabricated for example from dextran have been used for cultivating cells. Such supports can be obtained commercially from Pharmacia Fine Chemicals under the brand name Cytodex®. Such solid bio-supports, however, are not suitable for motive reactor systems such as vigorously stirred tanks and fluidized beds since substantially all of the cells are adherent to the surface of said supports and thus are exposed to impact stress and trauma during operation.

Porous inorganic microcarriers also are known and such supports potentially provide protection for the cells in motive applications since the cells populate the interior of the microcarriers. Unfortunately, inorganic microcarriers cannot be made with the proper combination of permeability and specific gravity to function well in all motive applications. For example, the porous fritted glass or cordierite supports described in Messing et al. U.S. Pat. No. 4,153,510 would typically exhibit specific gravities in aqueous suspension of less than about 1.3 if their void fractions are greater than about 80% (Note that void fractions for the Messing supports are not disclosed). Quite understandably, these supports are not suitable for all motive reactor systems where a higher specific gravity generally is needed to ensure high relative velocities for maximum rates of mass and energy transfer. Consequently, these supports have generally been relegated for use in packed bed applications.

An object of the present invention is to provide a microsponge containing immobilized bioactive materials suitable for use in motive reactor systems.

Another object of the present invention is to provide a microsponge suitable for immobilizing a large variety of organisms characterized by wide variations in size and their degree of attachment to solid supports.

A further object of the present invention is to provide a microsponge suitable for motive reactor systems which permits the continued growth and reproduction of immobilized organisms.

It also is an object of the present invention to provide a microsponge suitable for motive reactor systems which is conducive to maximizing the metabolic activity of immobilized organisms.

Yet another object of the present invention is to provide a method for continuously culturing organisms at high concentrations.

Still another object of the present invention is to provide a microsponge suitable for motive reactor systems which permits the culturing of organisms at high concentrations while accommodating either maximum growth rate or maximum metabolic activity.

These and other objects of this invention will become apparent from a consideration of the specification and appended claims.

SUMMARY OF THE INVENTION

The present invention pertains to a weighted collagen microsponge for immobilizing bioactive materials in motive bioreactor systems, said microsponge comprising a porous, biostable, highly cross-linked collagen matrix containing an inert weighting material, said collagen matrix having an open to the surface pore structure with an average pore size in the range of from about 1 micron to about 150 microns, with the pores of said matrix occupying from about 70 to about 98% by volume of the microsponge, said microsponge also having an average particle size of from about 100 microns to about 1000 microns and a specific gravity of above about 1.05.

DETAILED DESCRIPTION

Figure 1:
FIG. 1 is a photomicrograph showing a suitable collagen microsponge matrix of the present invention illustrating a fibrous structure.

The present invention is directed to a weighted collagen microsponge containing immobilized bioactive materials, particularly organisms, suitable for use in motive bioreactor systems. As used throughout the specification and claims, the term "bioactive material" broadly encompasses both enzymes and other chemical factors such as chelating agents, hormones, antibodies, etc., and organisms, i.e., microorganisms and the cells of higher organisms. The organisms may be either living or dead and may be derived without limitation from such diverse sources as bacteria, fungi, viruses, algae, yeasts, animal cells (tissue), e.g., mammals, insects, fish and plant cells. Since the invention has particular advantages when used for culturing organisms, it generally will be described with reference to such embodiments, although it is not to be so-limited.

The microsponge of this invention is formed of a highly crosslinked collagen. The modified (crosslinked) collagen of this invention is biocompatible (non-toxic) and is stable in service for an appropriate period of time, e.g., on the order of months. Biocompatibility refers to the ability of the collagen matrix material to support a viable culture of organisms without substantially adversely affecting any desired characteristic of the immobilized organisms, e.g., in the case of hybridomas, the collagen matrix material must not reduce the production of monoclonal antibodies. The stability or biostability of the matrix material refers to its ability to maintain its strength and integrity under in vitro conditions over the relevant time period for culturing the organism of interest. For example, in the case of a hybridoma culture for producing monoclonal antibodies, it is expected that the motive bioreactor would be operated continuously for three to six months or more. Thus, the matrix material should be biostable for this time period.

Collagen is a biodegradable polymer found in animals, including man. It has numerous uses in the medical art and in most applications is reconstituted and crosslinked into an insoluble form using various crosslinking agents, often glutaraldehyde. Unfortunately, many if not all of the commonly used crosslinking agents, particularly glutaraldehyde, which are unavoidably present in the crosslinked collagen, cause adverse biological effects and so are cytotoxic.

Recently, a new collagen-based matrix of improved biostability has been discovered. This collagen material is prepared without the conventional crosslinking agents. In this matrix, Type I, II or III collagen is crosslinked using a carbodiimide or a succinimidyl active ester and/or severe dehydration conditions at temperatures ranging from 50° to 200° C. Such crosslinked collagen typically has a molecular weight of from about $1 \times 10^6$ to in excess of $50 \times 10^6$. The molecular weight of the collagen between adjoining crosslinks varies from about 1000 to 100,000 via the formation of covalent bonds. Because of its resistance to degradation by collagenase and other proteinases, this crosslinked collagen has been found to be particularly suitable as the porous matrix of the microsponge. In fact, when used for the continuous culture of immobilized organisms, particularly hybridoma cells expressing monoclonal antibodies, microsponges made from this collagen material have exhibited some surprising properties. For example, hybridomas cultured with essentially protein-free medium are much more effective in producing monoclonal antibodies when immobilized on and/or in such collagen matrix microsponges than when such matrix is not present. Furthermore, microsponges made from the noted crosslinked collagen material appear to preferentially retain high concentrations of living (viable) cells and expel non-viable cells.

The preferred crosslinked collagen can be prepared from both soluble collagens and insoluble collagens of the Types I, II and III. The soluble collagens are prepared by limited enzymatic digestion and/or extraction of tissue enriched in such collagen types. Insoluble collagens are derived from the following typical sources: Type I collagen: bovine, porcine, chicken and fish skin, bovine and chicken tendon and bovine and chicken bones including fetal tissues; Type II collagen: bovine articular cartilage, nasal septum, sternal cartilage; and Type III collagen: bovine and human aorta and skin. For example, Type I collagen from bovine corium may be used. It is preferred to use Type I tendon collagen.

In order to be suitable for culturing high concentrations of organisms in motive reactor systems and allow for the transfer of nutrients to the immobilized organisms and the transfer of desired products from the microsponge, the collagen microsponge of the present invention must satisfy several functional requirements. The microsponge typically is in the shape of a bead and should have a particle size within the range of about 100 microns to 1000 microns, preferably from about 200 microns to 500 microns. At larger particle sizes the entire internal volume of the porous structure is not utilized effectively for producing the desired product by reaction between the immobilized bioactive material and the liquid medium contacted therewith, thus degrading the volumetric productivity of the motive reactor employing such microsponges. Smaller particle sizes present practical problems in preparing the microsponge and in operating the motive reactor.

Permeability of the microsponge is another important consideration. A microsponge's permeability is determined by the interrelationship of its porosity or void fraction and its pore structure. Void fraction is defined as the ratio of the volume of interstices of a material to the total volume occupied by the material and often is expressed as a percentage. In order to permit operation at high organism concentrations, the microsponge should have a void fraction of between about 70% and 98%. Preferably the void fraction of the collagen microsponge is greater than 85% and most desirably is greater than about 90%.

The microsponge also must possess an open to the surface pore structure. This allows for cell entry, without excessive shear forces, cell retention, subsequent cell growth, and expulsion of excess cell mass. For example in cases where the desired product is not secreted by the organisms, e.g., genetically engineered *E. coli* with a non-expressed rDNA product such as insulin, the organisms must be able to escape the microsponge as the immobilized colony expands by division. An open pore structure is essential if this process is to proceed on a continuous basis, without rupturing the microsponge structure. The desired organism product is recovered as an entrained component of the culture harvest liquor.

The microsponge should contain pores with an average size within the range of about 1 micron for the smallest microbes and for viruses, up to about 150 microns for large mammalian and plant cells. Generally, the pores of the microsponge must be at least as large as the smallest major dimension of the immobilized bioactive material but less than about 5 times the largest major dimension. Preferably, the pore size of the matrix is on the order of 1.5 to 3 times the average diameter of the organism or cell. If unknown, the smallest and largest major dimensions of an organism can be determined using known techniques. Applicants have found that the recited combination of particle sizes and pore sizes insure adequate mass transfer of constituents such as nutrients to the immobilized organisms, as well as adequate mass transfer of constituents, such as desired metabolites from the immobilized organisms.

For use in motive reactor systems, the collagen microsponge also must be weighted. The crosslinked collagen used as the matrix material in the present invention generally has a specific gravity of about 1.0 or less. For proper operation in a motive reactor, a specific gravity of above about 1.05, preferably above about 1.3 and most preferably between about 1.6 and 2.0 is desired. It has been found surprisingly that it is possible to obtain collagen microsponges of the proper specific gravity by introducing certain weighting additives into the microsponge without undesirably reducing its void fraction. The weighting additive must be substantially inert in the reactor environment and non-toxic to the immobilized organism, or must be suitably treated to render the additive non-toxic. Also, the weighting additive should not adversely affect the productivity of the immobilized organism. Generally, materials, such as metals and their alloys and oxides, and ceramics, having a specific gravity above about 4 and preferably above about 7 are used. Examples of suitable weighting additives for use in the broad practice of this invention are chromium, tungsten, molybdenum, cobalt, nickel, titanium and their alloys, e.g., Monel, 316 stainless, Vitalium (a cobalt alloy with chromium and molybdenum), titanium 6A1-4V (a titanium alloy with aluminum and vanadium) and Haynes Stellite Alloy 25 (a cobalt alloy with chromium nickel, tungsten and manganese). Many of these materials, however, may not be compatible with certain organisms and routine experimentation will be necessary to assess toxicity for any application. For example, titanium is the weighting material of choice with hybridomas, since most other metals are cytotoxic.

The weighting additive can be introduced into and dispersed throughout the microsponge as a finely divided powder, with most particles having a size on the order of 10 to 40 microns. However, to minimize the surface area of the weighting additive, it is desirable to employ it as a solid core in the microsponge. Sufficient weighting material is added to yield a microsponge with the desired specific gravity. For example, about a 50 micron diameter core of a weighting additive having a specific gravity of about 7.0 coated with a 50 micron thick layer of collagen having an average pore size of 20 to 40 microns and a void fraction of about 99% yields a microsponge with a specific gravity of about 1.7 having an overall void fraction of about 85%. Such a microsponge is particularly suitable for use in an aerobic motive reactor systems.

Finally, for motive applications the collagen microsponge should exhibit the proper resistance to attrition. A charge of microsponges preferably should have a useful life on the order of three to six months or more. Typically, the microsponges should exhibit not greater than about a 10% loss in volume after three months of operation.

Normally, organisms exhibit wide variation in their degree of attachment to solid supports. Certain organisms, for example, readily cling or attach to a wide variety of supports, including both organic and inorganic materials, while others will only attach to supports of biological origin (attachment-dependent organisms). Other organisms exhibit little direct attachment to any support material (attachment-independent organisms). The collagen microsponge of the present invention, because it is prepared from a natural polymer and because of its permeability (porosity and pore structure) should be suitable for immobilizing substantially all types of organisms.

In fact, as noted in more detail below, it even is possible to tailor the micro-structure or configuration of the microsponge to best accommodate the attachment tendency of the immobilized organism. For example, microsponges having the wire-mesh structure (FIG. 1) can be employed in conjunction with attachment-independent organisms, while microsponges exhibiting a leafy structure (FIG. 2) can be used with attachment dependent organisms.

Any suitable procedure used by the prior art for immobilizing such organisms on microsponges can be used in the present invention including such techniques as adsorption and chemical coupling. For example, in the case of certain organisms it will only be necessary to mix the collagen microsponges in a broth inoculated with the specific organism. After a short period of time, the organism will colonize the microsponges and become entrapped in their pores. In the case of some organisms such as fibroblasts and hybridomas, it also may be desirable to coat the microsponge with attachment-promoting materials such as fibronectin, polylysine and anti-hybridoma antibodies prior to inoculation. Other techniques, such as applying a net charge to the surface of the microsponge, also can be used to enhance immobilization.

As will be recognized by those skilled in this art, in the broad practice of the present invention, the procedure used for bringing the immobilized bioactive material into direct contact with a liquid reagent stream such as a growth supporting medium for culturing of immobilized organisms is not critical and any of the numerous arrangements available in the prior art including such well known apparatus as stirred tank reactors, fixed bed reactors, fluidized bed reactors and moving bed reactors and the like could be used. Generally, when culturing organisms the microsponges are charged to a suitable reactor and mixed therein with a nutrient broth and an inoculum of the organism. The microsponges should be completely submerged. The microsponges are incubated so that the organisms grow and colonize the porous matrix of the microsponge. Fresh nutrient broth along with other materials necessary for growth, such as oxygen in the case of aerobic organisms, are supplied in a continuous manner to the reactor and harvest liquor containing the biochemical product of interest is recovered. The biochemical product may comprise a primary or secondary metabolite of an immobilized organism, excess biomass generated by an immobilized organism containing for example a non-secretory product, an immobilized enzyme catalyzed reaction product or the like.

A particular advantage of the microsponge of the present invention is that it can be used in a mixed or motive system such as a fluidized bed reactor. As used herein, the term "motive reactor" refers to reactor systems in which relative motion between the microsponge and the fluid medium is provided in part by imparting motion to the microsponges themselves. Such reactor systems substantially enhance mass and energy transfer. A particularly preferred motive reactor system is described in co-pending U.S. patent application Ser. No. 706,872 filed on Feb. 28, 1985, now abandoned in the names of Robert C. Dean, Jr., Peter V. Grela and Subhash B. Karkare.

To prepare the highly crosslinked collagen microsponge, a suitable collagen source first is milled to a small "fiber" size. Generally, the collagen is milled (e.g., using a Wiley mill) to obtain particles (fibers) with a maximum dimension on the order of about 200 microns. Preferably, the collagen source material is milled (i.e., dry ground) to yield fibers having a diameter on the order of 1 to 50 microns and a length no greater than about 200 microns. Proper milling of the collagen source material is important for obtaining microsponges of the desired structure.

The milled collagen then is formed into a collagen-based solution or dispersion, i.e., a soluble collagen dissolved in a solvent, or an insoluble collagen dispersed in a solvent by admixture with a suitable solvent, particularly acids such as dilute hydrochloric acid, dilute acetic acid or the like. In the present invention organic acids are particularly preferred, including acetic acid, lactic acid, proprionic acid, butyric acid and the like. Certain long chain fatty acids also could be used. The collagen is mixed into the liquid (solvent) using standard mixing equipment. Preferably, in the case of a collagen dispersion the mixing is accomplished with a high level of agitation using, for example, a Waring blender, so as to produce microfibers of the collagen. The mixture of collagen and solvent typically comprises between about 0.5% to about 1.5% by weight of the collagen. The mixture preferably exhibits a pH in the range of about 2.0 to about 4.0. A pH in the range of 1.0 to 2.0 may also be used as long as the temperature of the mixture is sufficiently reduced (e.g., about 4° C.) to avoid denaturization of the collagen.

Next, the weighting additive is blended with the collagen-liquid mixture and the composite mixture is formed into small droplets and rapidly solidified by freezing at a temperature below about 0° C. and preferably below about −30° C. to form particles of the desired size. Any known technique for producing small particles can be employed in carrying out the present invention. Suitable techniques include, inter alia, pressure or air-shear spraying, emulsification techniques, droplet formation using Raleigh liquid jet instability techniques, extrusion techniques, droplet formation using gravity or centrifugal forces, electrostatic droplet formation, and droplet formation using inertial forces. For example, suitable sized particles have been prepared using inertial forces to form small droplets at the orifice of a vibrating needle. The droplets can be frozen by allowing them to fall into a cryogenic bath of liquid nitrogen. Obviously other chilling baths for freezing the droplets could be used, e.g., chilled ethanol. Also, larger sized particles formed by freezing possibly could be reduced to the desired particle size by such destructive techniques as grinding and the like. Still additional techniques such as various coating methodologies, could be used to form microsponges having a solid core of the weighting additive. In this case a shell of the collagen matrix would surround the weighted core. Those skilled in the art will recognize other techniques suitable for forming small particles of the types described above and the present invention is not intended to be limited to any specific technique.

The pore size and structure of the collagen microsponge is influenced by a variety of factors. For example, changes in the collagen concentration appear to affect pore size, with higher collagen concentration tending to yield smaller pore dimensions. The pH of the mixture and the specific acid used in preparing the mixture also affect the pore size and structure of the resultant microsponge. For example, it has been found that too low a pH tends to significantly limit the pore dimensions of the microsponge while higher pHs cause a distinct collagen phase to separate from the original solution or dispersion thereby preventing the formation of a porous structure and when a finely divided weighting additive is used it tends to remain in the dispersed phase. The rate of freezing also appears to influence the structure of the microsponge and the structure also will vary with changes in collagen type.

Thereafter, the frozen composite is vacuum freeze-dried preferably using conventional equipment operating at a vacuum of more than about 50 millitorr and at a temperature in the range of about 22° C. to −100° C. The combination of freezing and drying is referred to as lyophilization.

The freeze-dried collagen matrix composite then is treated so as to crosslink the collagen. The collagen can be crosslinked using either chemical crosslinking agents preferably selected from the group consisting of a carbodiiamide or N-hydroxy succinimide-derived active esters (succinimidyl active esters), by severe dehydration at an elevated temperature or by a combination of these treatments. The strength and biostability of the collagen matrix so-prepared is influenced by the degree of crosslinking introduced through such treatment. These crosslinking methods provide a collagen matrix that is surprisingly resistant to collagenase and other enzymatic degradation thereby making these materials particularly suitable for culturing organisms. Examples of carbodiiamides which can be used in the chemical treatment are cynamide and 1-ethyl-3-(3-dimethylaminopropyl)-carbodiiamide hydrochloride. Suitable bifunctional succinimidyl active esters include bifunctional N-hydroxy succinimide, 3,3'-dithio(sulfosuccinimidyl) proprionate and bis(sulfosuccinimidyl) suberate. When using such chemical crosslinking agents, the dry collagen matrix material is immersed in a solution of the crosslinking agent at about room temperature for a period of time of from about 2 to 96 hours. The solution of crosslinking agent may contain from about 0.1 to about 15% (weight per volume) of the crosslinking agent. Alternatively, the crosslinking agent could be added to the original solution or dispersion of the collagen source.

To crosslink the collagen matrix using severe dehydration, the microsponge is subjected to a vacuum of about 50 millitorr or more for a period of time of from about 2 to about 96 hours at a temperature in the range of about 50° C. to about 200° C., e.g., about 100° to 110° C.

As noted above, the two treatments also can be used in combination and it is preferred to use a severe dehydration treatment followed by chemical treatment to crosslink the collagen matrix. Generally, however, in those cases where chemical treatment precedes the dehydration treatment the crosslinking agent should be added directly to the original collagen solution or dispersion prior to formulation of the matrix particles and lyophilization in order to facilitate subsequent vacuum dehydration treatment. Also as noted above the strength and biostability of the collagen matrix is influenced by the degree of crosslinking introduced through such treatment. These crosslinking methods provide a collagen matrix that is surprisingly resistant to collagenase and other enzymatic degradation thereby making these materials particularly suitable for culturing organisms. Whenever chemical treatment is used, the collagen matrix should be washed extensively prior to further use in order to remove any excess crosslinking agent. Further information concerning the procedure for preparing the highly crosslinked collagen can be obtained from U.S. Pat. No. 4,703,108 issued Oct. 27, 1987, based on U.S. patent application Ser. No. 843,828 filed on Mar. 26, 1986, which is a continuation of U.S. patent application Ser. No. 593,733 filed on Mar. 17, 1984, now abandoned, in the names of Frederick H. Silver, Richard A. Berg, David E. Birk, Kevin Weadock and Conrad Whyne and entitled "Biodegradable Matrix and Methods for Producing Same," the disclosure of which is incorporated herein by reference.

After thoroughly washing the crosslinked collagen matrix in ultra-pure water, the microsponges then may be sterilized using conventional sterilization techniques. A particular advantage of the collagen microsponges is that they are manufactured separate from the step of organism immobilization and as a result they can be properly sterilized prior to being inoculated or stored. Preferably, the microsponges are sterilized using gamma irradiation. Ethylene oxide also may be used as an alternative, as may additional sterilization procedures known to those skilled in the art, as long as the important characteristics of the microsponge are not compromised. Obviously, when sterilizing the microsponges using ethylene oxide the particles must be thoroughly ventilated in order to remove all traces of this sterilizing agent before subsequently using the microsponges for culturing organisms. It also has been discovered that the severe dehydration treatment for an extended time at an elevated temperature used to crosslink the collagen may satisfactorily sterilize the microsponge, thus obviating any additional treatment.

Preferably, the sterilized microsponges are aseptically packaged for delivery to the ultimate consumer. The user simply places the microsponges into a previously sterilized reactor, adds the proper nutrients and inoculum and initiates operation. In a preferred embodiment, the package actually comprises a disposable reactor vessel having the necessary connections for feeding a nutrient stream, for removing a harvest liquor and for ancillary operations, as needed, such as heat exchange, oxygenation and process control. For a fluidized bed reaction, the vessel also would contain a suitably designed distribution plate. Such a pre-packaged disposable reactor vessel may have a volume between about 0.1 liter and 10 liters. In this case, the user of the reactor simply integrates it into the process equipment consisting of pumps, valves, piping, heat and gas exchangers and various instrumentation and related probes and begins operation. Providing a disposable reactor, pre-packaged with the microsponges sterilized and ready for use, significantly simplifies start-up procedures for culturing organisms, particularly when changing from one culture to another.

Figure 2:
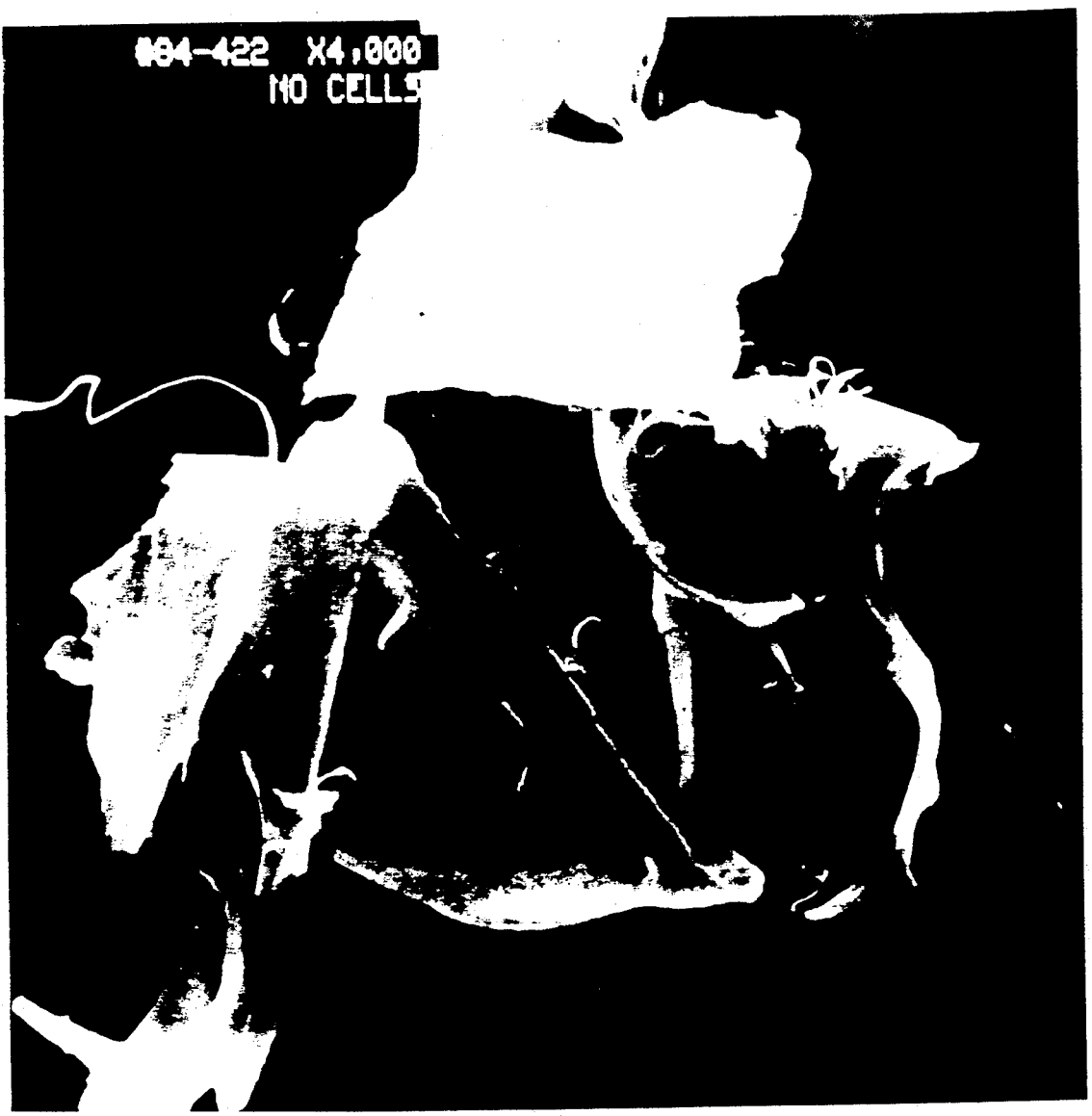
FIG. 2 is a photomicrograph of another collagen microsponge matrix according to the present invention illustrating a leafy structure.

Although not completely understood, it has been observed that variations in process parameters lead to important variations in the structure or configuration of the highly crosslinked collagen matrix itself. FIGS. 1 and 2, which are photomicrographs of the collagen matrix prepared using the techniques described above, illustrate these different structures. The photomicrographs of FIGS. 1 and 2 were obtained using scanning electron microscopy. FIG. 1 illustrates a collagen matrix having substantially a wire-mesh structure. In this structure, the diameter of the fiber network typically is on the order of about 1 micron. This structure is particularly desirable for attachment-independent type organisms such as hybridomas. In this matrix, such organisms become trapped in and on the matrix structure. FIG. 2 illustrates a leaf-type matrix structure. The leaves of this structure typically have a thickness on the order of about 1 micron. This stucture is particularly suitable for attachment-dependent cells such as fibroblast cells. Currently, it is believed that the rate of chilling (freezing) the droplets in the bead making process influences the morphology of the collagen microsponge.

The following examples are intended to more fully illustrate the invention without acting as a limitation on its scope.

EXAMPLE 1

This example describes the preparation of microsponges of the highly crosslinked collagen matrix material.

Partially purified tendon collagen was milled to obtain fibers having a length of less than about 200 microns and a diameter of between about 5 and 50 microns using a Wiley Mill obtained from VWR Scientific. An amount of milled collagen material then was mixed with a solution of acetic acid using a Waring blender so as to produce a collagen-based dispersion having a pH of about 3.0 and about 1.0% (by weight) of collagen. Then, an inert weighting material, titanium, was added to the collagen-based dispersion as a fine powder having particle sizes within the range of about 5 to about 180 microns.

The composite mixture then was formed into solid particles by first producing small droplets of the composite mixture. Droplets were produced by flowing the composite mixture through a vibrating hollow needle having an internal diameter of about 1.3 millimeters vibrated at a frequency of about 90 Hz. The droplets fell into a cryogenic bath of liquid nitrogen and were rapidly frozen. The frozen droplets of the composite mixture then were vacuum dried using a Virtis Freezemobile Lyophilizer Model 6 at a vacuum of about 10 millitorr for about 48 hours.

After such lyophilization, the dried microsponges were subjected to a severe dehydration (dehydrothermal treatment) at a temperature of about 100° C. under a vacuum of about 10 millitorr for about 72 hours using a VWR Scientific drying oven. The microsponges then were treated with a 1.0% (by weight) solution of cyanamide as a chemical crosslinking agent at a pH of about 5.5 for about 24 about 20° C.

The highly crosslinked microsponges then were thoroughly washed for about 24 hours using ultra-pure water, were dried and then sterilized by gamma irradiation. The microsponges had particle sizes within the range of about 200 to 800 microns, a void fraction on the order of about 77%, pore sizes on the order of about 20 microns, and a specific gravity on the order of about 1.1. The microsponges had a wire mesh micro-structure.

EXAMPLE 2

The microsponges of Example 1 can be used to support the growth of hybridoma cells. In particular, about 300 ml of the microsponges can be contained in a 600 ml reactor vessel. The microsponges can be inoculated with the hybridoma cells and cultured using a suitable nutrient medium. The reactor can be operated at a solids concentration of about 25–40%, while the content of the reactor is vigorously agitated. A nutrient medium such as Delbecko Modified Eagle medium with 10% fetal calf serum can be passed into the reactor in a continuous manner and a product stream containing the monoclonal antibodies can be recovered at a substantially equivalent flow rate.

It will be obvious to one of ordinary skill that numerous modifications may be made without departing from the true spirit and scope of the invention which is to be limited only by the appended claims.

We claim:

1. A weighted collagen microsponge for immobilizing bioactive materials in motive bioreactor systems, said microsponge comprising a porous, biocompatible, biostable, insoluble highly crosslinked collagen matrix containing an inert weighting material, said collagen matrix having an open to the surface pore structure with an average pore size in the range of from about 1 micron to about 150 microns, the pores of said matrix occupying from about 70 to about 98% by volume of the microsponge, said microsponge also having an average particle size of from about 100 to about 1000 microns and a specific gravity above about 1.05.

2. The microsponge of claim 1 having immobilized therein bioactive material selected from the group consisting of enzymes, dead cells and living cells.

3. The microsponge of claim 1 wherein said inert weighting material is selected from the group consisting of metals, metal alloys, metal oxides and ceramics.

4. The microsponge of claim 3 wherein said weighting material has a specific gravity of above about 4.0 and said microsponge has a specific gravity of above about 1.3.

5. The microsponge of claim 4 wherein said inert weighting material is dispersed throughout said collagen matrix as finely divided powder.

6. The microsponge of claim 4 wherein said weighting material is centrally disposed as a solid core about which said collagen matrix is formed.

7. The microsponge of claim 4 wherein said inert weighting material is selected from the group consisting of chromium, tungsten, cobalt, molybdenum, titanium, nickel and alloys thereof.

8. The microsponge of claim 7 wherein said weighting material is titanium and said microsponge has hybridoma cells immobilized therein.

9. The microsponge of claim 2, wherein the cells are microorganisms.

10. A bioreactor system comprising a reactor vessel having aseptically sealed therein a plurality of sterilized weighted collagen microsponges for immobilizing bioactive materials in motive bioreactor systems, said microsponges comprising a porous, biocompatible, biostable, insoluble highly crosslinked collagen matrix containing an inert weighting material, said collagen matrix having an open to the surface pore structure with an average pore size in the range of from about 1 to about 150 microns, the pores of said matrix occupying from about 70 to about 98% by volume of the microsponge, said microsponge also having an average particle size of from about 100 to about 1000 microns and a specific gravity of above about 1.05.

11. The biorector system of claim 10 wherein said reactor has a volume between about 0.1 to 10 liters.

12. The bioreactor system of claim 11 wherein said reactor is a fluidized bed reactor, having a fluid distribution plate.

13. A process for performing a bioreaction comprising immobilizing a bioactive material in weighted collagen microsponges comprising a porous, biocompatible, biostable, insoluble highly crosslinked collagen matrix containing an inert weighting material, said collagen matrix having an open to the surface pore structure with an average pore size in the range of from about 1 micron to about 150 microns, the pores of said matrix occupying from about 70 to about 98% by volume of the microsponge, said microsponge also having an average particle size of from about 100 to about 1000 microns and a specific gravity above about 1.05; retaining the microsponges having said immobilized bioactive material in a suitable reactor vessel; passing a liquid reagent stream into said reactor in direct contact with said microsponges; agitating the mixture of said microsponges and said reagent stream and recovering the biochemical reaction products from said reactor.

14. The process of claim 13 wherein said bioactive material is organisms, the microsponges are incubated to promote growth and colonization of said microsponges by said organisms, said reagent comprises nutrient media for promoting the growth and metabolism of said organisms, and wherein said product comprises metabolites of said organisms.

15. The process of claim 13 wherein said bioactive material is organisms and the recovered product comprises free organisms which have escaped from said microsponges.

16. The process of claim 14 wherein said organisms comprise hybridomas and said product comprises monoclonal antibodies.

17. The process of claim 16 wherein said reactor vessel comprises a fluidized bed reactor.

18. The process of claim 14 wherein said organisms comprise mammalian cells and said products comprise mammalian cell products.

19. The process of claim 14 wherein said organisms are genetically engineered microbial cells and said product comprises secreted protein products.

20. The process of claim 15 wherein said organisms are genetically engineered microbial cells and said product comprises said organisms containing a non-secreted protein product.

* * * * *